United States Patent
Seo et al.

(10) Patent No.: US 11,612,327 B2
(45) Date of Patent: Mar. 28, 2023

(54) METHOD AND SYSTEM FOR CONTINUOUSLY MEASURING ANIMAL BODY TEMPERATURE

(71) Applicant: SB Solutions Inc., Ulsan (KR)

(72) Inventors: Seungup Seo, Ulsan (KR); Namhwan Sung, Ulsan (KR); Hae Dong Lee, Ulsan (KR); Seong Mun Kim, Ulsan (KR); Ji Woong Song, Ulsan (KR); Jagannath Malik, Ulsan (KR)

(73) Assignee: SB SOLUTIONS INC., Ulsan (KR)

( * ) Notice: Subject to any disclaimer, the term of this patent is extended or adjusted under 35 U.S.C. 154(b) by 0 days.

(21) Appl. No.: 17/399,972

(22) Filed: Aug. 11, 2021

(65) Prior Publication Data
US 2022/0386876 A1  Dec. 8, 2022

(30) Foreign Application Priority Data
Jun. 2, 2021  (KR) .................. 10-2021-0071306

(51) Int. Cl.
*A61B 5/01* (2006.01)
*A61B 5/00* (2006.01)
(Continued)

(52) U.S. Cl.
CPC ................ *A61B 5/01* (2013.01); *A61B 5/002* (2013.01); *A61B 5/0008* (2013.01);
(Continued)

(58) Field of Classification Search
CPC ....... H02J 50/00–90; A61B 2560/0219; A61B 5/01; A61B 5/0008; A61B 5/002;
(Continued)

(56) References Cited

U.S. PATENT DOCUMENTS 7,203,551 B2 *  4/2007  Houben ............. A61N 1/36542
                                                  607/116
9,995,718 B1 *  6/2018  Novotny ............ G01N 29/2437
                        (Continued)

FOREIGN PATENT DOCUMENTS

JP     2000-350705      12/2000
KR  10-2016-0120396 A   10/2016
                        (Continued)

OTHER PUBLICATIONS

Texas Instruments, "Sine-Wave Oscillator" Application Report SLOA060 (Year: 2001).*
(Continued)

*Primary Examiner* — David J. McCrosky
(74) *Attorney, Agent, or Firm* — Christensen O'Connor Johnson Kindness PLLC

(57) ABSTRACT

A method and system for continuously measuring animal body temperature are disclosed. The system includes: an external device for transmitting wireless power into an animal's body from outside the animal's body; and an implant device inserted into the animal's body, that periodically measures the animal's body temperature by a temperature sensor by using battery power and stores continuous body temperature information in storage, and that, when wireless power is received from the external device, sends the continuous body temperature information stored in the storage to the external device by using the received wireless power.

18 Claims, 10 Drawing Sheets

(51) Int. Cl.
  *H02J 50/80* (2016.01)
  *H02J 50/10* (2016.01)
(52) U.S. Cl.
  CPC .......... *A61B 5/0022* (2013.01); *A61B 5/0031* (2013.01); *H02J 50/10* (2016.02); *H02J 50/80* (2016.02); *A61B 2503/40* (2013.01); *A61B 2560/0214* (2013.01)
(58) Field of Classification Search
  CPC . A61B 5/0022; A61B 5/0031; A61B 2503/40; A61B 2560/0214
  See application file for complete search history.

(56) References Cited

U.S. PATENT DOCUMENTS

| | | | | |
|---|---|---|---|---|
| 10,721,178 | B2 * | 7/2020 | Zhang | A61N 1/37252 |
| 2007/0296393 | A1 * | 12/2007 | Malpas | H02J 50/402 |
| | | | | 323/355 |
| 2021/0361945 | A1 * | 11/2021 | Chin | A61N 1/3704 |

FOREIGN PATENT DOCUMENTS

| | | | |
|---|---|---|---|
| KR | 10-2018-0135694 A | 12/2018 | |
| KR | 10-2086430 B1 | 3/2020 | |
| KR | 10-2020-0077883 A | 7/2020 | |
| KR | 10-2020-0145710 A | 12/2020 | |
| WO | WO-2020256498 A1 * | 12/2020 | ............... A61B 5/05 |
| WO | WO-2020256500 A1 * | 12/2020 | ......... A61B 5/14532 |
| WO | WO-2021201528 A1 * | 10/2021 | |

OTHER PUBLICATIONS

Machine translation of WO 2021/201528 A1 (Year: 2021).*
Raymaps, "Frequency Estimation Using Zero Crossing Method". Retrieved from https://www.raymaps.com/index.php/frequency-estimation-using-zero-crossing-method/ (Year: 2020).*
International Search Report dated Aug. 16, 2022, issued in corresponding International Patent Application No. PCT/KR2022/006403, filed Jun. 2, 2021, 3 pages.

* cited by examiner

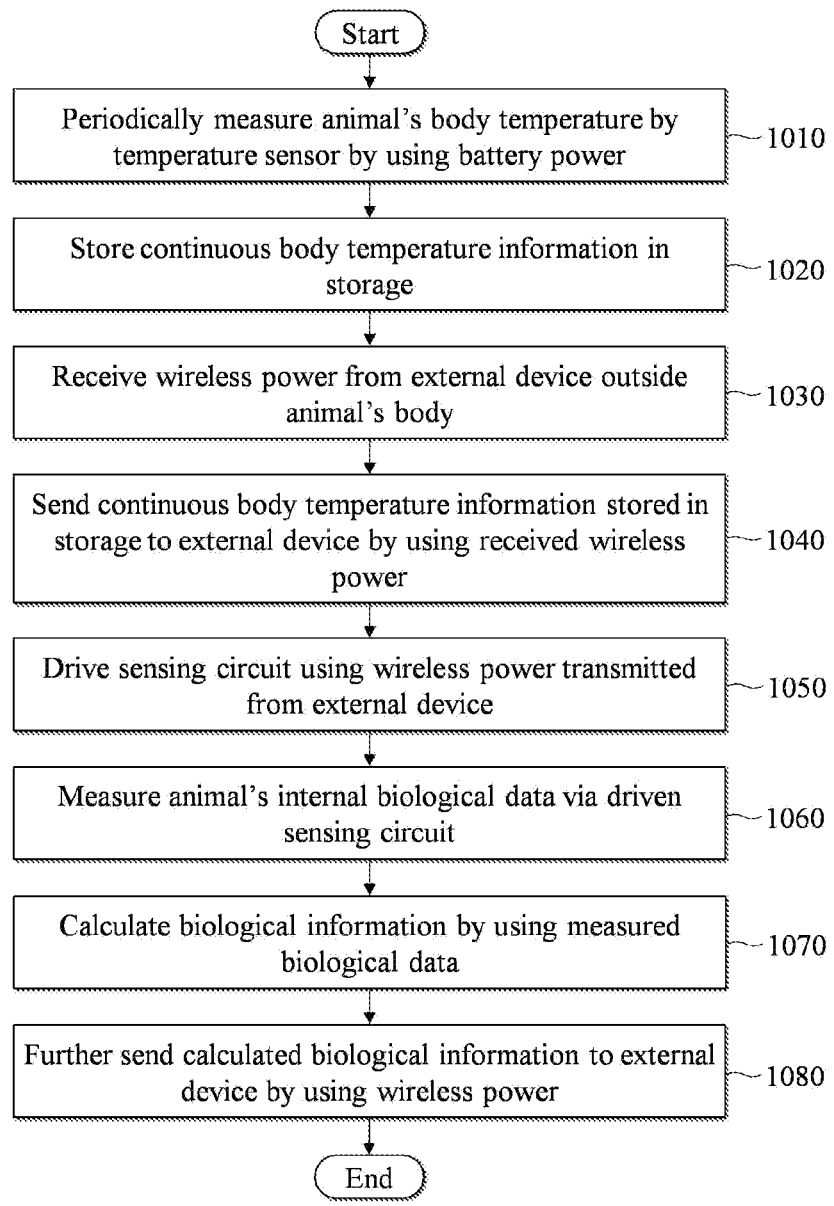

METHOD AND SYSTEM FOR CONTINUOUSLY MEASURING ANIMAL BODY TEMPERATURE

CROSS-REFERENCES TO RELATED APPLICATIONS

This application is based on and claims priority under 35 U.S.C. 119 to Korean Patent Application No. 10-2021-0071306, filed on Jun. 2, 2021, in the Korean Intellectual Property Office, the disclosures of which is herein incorporated by reference in their entireties.

TECHNICAL FIELD

The present disclosure relates to a method and system for continuously measuring animal body temperature.

BACKGROUND OF THE INVENTION

Generally, the body temperature of animals such as livestock is measured individually, one by one, by using a thermometer, or are estimated by using body temperature image information captured in livestock barns.

However, in the case of using a thermometer, it takes too much time to measure the body temperature of each individual animal, and measuring the body temperature of animals is really hard because they are supposed to incessantly move. Moreover, body temperature measurement using image capturing is only for measuring the temperature of the outermost surface of an animal's body, and does not provide accurate measurement of the animal's core body temperature.

The above information is only for enhancement of understanding and therefore it may contain information that does not form part of the prior art that is known to a person of ordinary skill in the art.

PRIOR ART DOCUMENT

Korean Patent Application Registration No. 10-2086430

SUMMARY

This summary is provided to introduce a selection of concepts in a simplified form that are further described below in the Detailed Description. This summary is not intended to identify key characteristics of the claimed subject matter, nor is it intended to be used as an aid in determining the scope of the claimed subject matter.

The present disclosure provides a method and system for continuously measuring animal body temperature, in which an implant device inserted into an animal's body is able to continuously measure body temperature within an animal's body and minimize the battery power consumption of the implant device, by continuously measuring and storing the animal's body temperature information using battery power and sending the stored continuous body temperature information to an external device outside the animal's body using wireless power from the external device.

An exemplary embodiment of the present disclosure provides a system for continuously measuring animal body temperature, the system including: an external device for transmitting wireless power into an animal's body from outside the animal's body; and an implant device inserted into the animal's body, that periodically measures the animal's body temperature by a temperature sensor by using battery power and stores continuous body temperature information in storage, and that, when wireless power is received from the external device, sends the continuous body temperature information stored in the storage to the external device by using the received wireless power.

According to one aspect, the implant device may receive the wireless power using near field communication (NFC) and send the continuous body temperature information to the external device via the NFC.

According to another aspect, the implant device may include Bluetooth low energy (BLE) or ultra low power (ULP) WiFi, operate under control of a micro controller unit (MCU) included in the BLE or ULP WiFi, and send the continuous body temperature information to the external device via an antenna connected to the BLE or the ULP WiFi.

According to another aspect, the implant device may drive a sensing circuit using the wireless power received from the external device, measure the animal's internal biological data via the driven sensing circuit, calculate biological information using the measured biological data, and further send the calculated biological information to the external device by using the wireless power.

According to another aspect, the implant device may calculate the biological information by further using current body temperature information, among the continuous body temperature information.

According to another aspect, the sensing circuit may be an oscillator-type sensing circuit and include both a signal source and a detector.

According to another aspect, the implant device may generate a fringing field by using the sensing circuit, measure a change in a resonance frequency generated by an oscillator based on a change in capacitance caused by a change in an analyte in the fringing field area, and measure the characteristics of the change in the analyte in the fringing field in response to the change in the resonance frequency.

According to another aspect, the implant device may generate the fringing field by a fringing-field capacitor of the oscillator which is included as the sensing circuit.

According to another aspect, the implant device may generate a periodic oscillation signal by using a feedback network, which includes the fringing-field capacitor of the oscillator, as the sensing circuit, and a frequency selective filter, and which passes back some portion of an output signal as input to provide a desired phase shift.

According to another aspect, the implant device may measure the characteristics of the change in the analyte within the fringing field in response to the change in the resonance frequency by measuring a change in capacitance caused by a change in permittivity by means of a sensing part including a material with a dielectric constant.

According to another aspect, the battery may be configured to be charged by the wireless power.

Another exemplary embodiment of the present disclosure provides an implant device inserted into an animal's body to measure body temperature, the implant device including: a controller; a battery; temperature sensor; and a transmission/reception part, wherein the controller periodically measures the animal's body temperature by the temperature sensor by using the battery's power and stores continuous body temperature information in storage, and, when wireless power is received from an external device, sends the continuous body temperature information stored in the storage to the external device via the transmission/reception part by using the received wireless power.

According to one aspect, the transmission/reception part may include near field communication (NFC), and the controller may receive the wireless power using the NFC and send the continuous body temperature information to the external device using the NFC.

According to another aspect, the transmission/reception part may include a transmission part and a reception part, wherein the transmission part includes Bluetooth low energy (BLE) or ultra low power (ULP) WiFi, and the controller is implemented by a micro controller unit (MCU) included in the BLE or ULP WiFi to send the continuous body temperature information to the external device via an antenna connected to the BLE or the ULP WiFi.

According to another aspect, the implant device may further include a sensing circuit, wherein the controller drives a sensing circuit using the wireless power received from the external device, measures the animal's internal biological data via the driven sensing circuit, calculates biological information using the measured biological data, and further sends the calculated biological information to the external device via the transmission/reception part by using the wireless power.

According to another aspect, the battery may be configured to be charged by the wireless power.

Another exemplary embodiment of the present disclosure provides a method for continuously measuring animal body temperature by an implant device inserted into an animal's body, the method including the steps of: periodically measuring the animal's body temperature by a temperature sensor by using battery power; storing continuous body temperature information in storage; receiving wireless power from an external device outside the animal's body; and sending the continuous body temperature information stored in the storage to the external device by using the received wireless power.

According to one aspect, the receiving step may include receiving the wireless power using near field communication (NFC), and the transmitting step may include sending the continuous body temperature information to the external device via the NFC.

According to another aspect, the implant device may include Bluetooth low energy (BLE) or ultra low power (ULP) WiFi and operate under control of a micro controller unit (MCU) included in the BLE or ULP WiFi, wherein, in the transmitting step, the implant device sends the continuous body temperature information to the external device via an antenna connected to the BLE or the ULP WiFi.

According to another aspect, the method may further include the steps of: driving a sensing circuit using the wireless power received from the external device; measuring the animal's internal biological data via the driven sensing circuit; calculating biological information using the measured biological data; and further sending the calculated biological information to the external device by using the wireless power.

Since an implant device inserted into an animal's body continuously measures and stores the animal's body temperature information using battery power and sends the stored continuous body temperature information to an external device outside the animal's body using wireless power from the external device, it is possible to continuously measure the animal's body temperature within the body and minimize the battery power consumption of the implant device.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 10 is a flowchart illustrating an example of a method for continuously measuring animal body temperature by an implant device according to an embodiment of the present disclosure.

DESCRIPTION OF EXEMPLARY EMBODIMENTS

Figure 1:
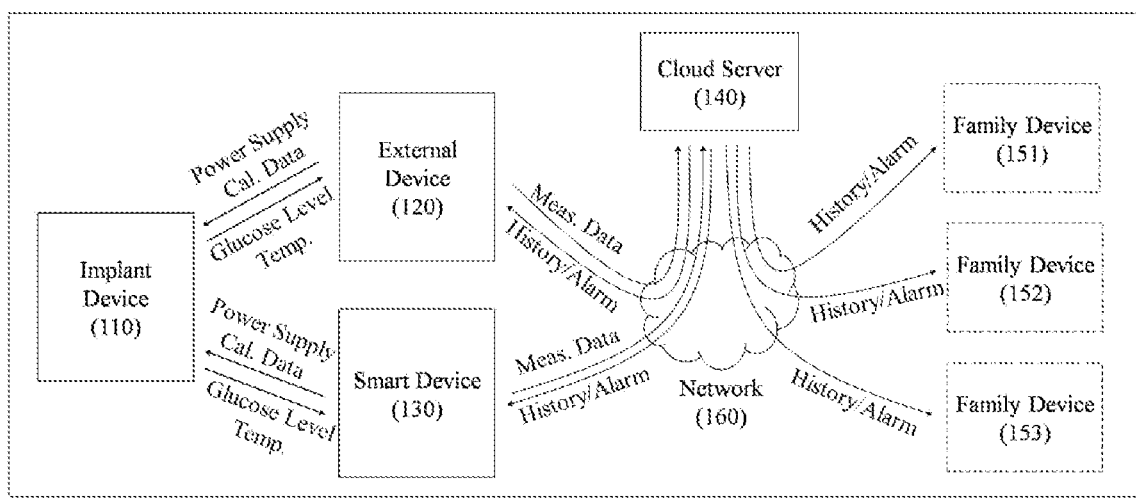
FIG. 1 is a view illustrating an example of a system for continuously measuring animal body temperature according to an embodiment of the present disclosure.

While illustrative embodiments have been illustrated and described, it will be appreciated that various changes can be made therein without departing from the spirit and scope of the invention.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessive unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the gist of the embodiment unnecessarily vague.

Furthermore, in describing components of an embodiments, terms, such as a first, a second, A, B, (a), and (b), may be used. Such terms are used only to distinguish one component from the other component, and the essence, order, or sequence of a corresponding component is not limited by the terms. When it is said that one component is "connected", "combined", or "coupled" to the other component, the one component may be directly connected or coupled to the other component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

FIG. 1 is a view illustrating an example of a system for continuously measuring animal body temperature according to an embodiment of the present disclosure. The system for continuously measuring animal body temperature according to this embodiment may include an implant device 110, an external device 120, a smart device 130, a cloud server 140, and a plurality of family devices 151 to 153. In this case, in some embodiments, only either the external device 120 or the smart device 130 may be included. The external device 120 and/or the smart device 130 may communicate with the cloud server 140 over a network 160. Also, in some embodiments, the plurality of family devices 151 to 153 may be omitted. Meanwhile, although FIG. 1 depicts three family devices as is the case with the plurality of family devices 151 to 153, the number of family devices is not limited to three.

The implant device 110 may be inserted into an animal's body, and may measure the animal's continuous body temperature information and send it to the external device 120 and/or the smart device 130. In this case, the implant device 110 may include a battery and a temperature sensor, in order to continuously measure body temperature information within the animal's body, and, at the same time, may store continuous body temperature information in storage and then send the continuous body temperature information stored in the storage to the external device 120 or the smart device 130 by using wireless power received from the external device 120 or the smart device 130, in order to maximize the battery life.

Moreover, in some embodiments, the implant device 110 may include both a signal source that outputs signals for measuring biological information and a detector that detects reflected and returned signals to additionally provide the animal's body temperature information such as blood sugar levels. The implant device 110 may include an oscillator-type sensing circuit, and the signal source and the detector may be included in the sensing circuit. An operation for measuring and sending biological information may be performed based on power received wirelessly from the external device 120 or the smart device 130, in order to reduce the battery power consumption of the implant device 110.

The implant device 110 may receive and use calibration data (Cal. Data) from the external device 120 or the smart device 130. For example, the implant device 110 may output signals via a signal source by using power received wirelessly from the external device 120 or the smart device 130, and may detect reflected and returned signals by using a detector. At this point, the implant device 110 may calculate biological information by using sensing data, which is detected data, and received calibration data, and may send the calculated biological information to the external device 120 or the smart device 130.

The external device 120 and the smart device 130 may basically serve the same functions of transmitting wireless power to the implant device 110 and collecting data from the implant device 110. Moreover, the external device 120 or the smart device 130 may upload data measured and collected by the implant device 110 to the cloud server 140 over the network 160, and the cloud server 140 may store and manage the uploaded data by user and/or by animal type. For example, the cloud server 140 may send to the external device 120 or the smart device 130 a history of uploaded data or an uploaded data-based notification, based on the data uploaded by user and/or by animal type. To this end, the cloud server 140 may include a function for analyzing uploaded data.

While FIG. 1 illustrates the external device 120 and the smart device 130 separately, an external device to be described later may refer to either the external device 120 or the smart device 130.

Figure 2:
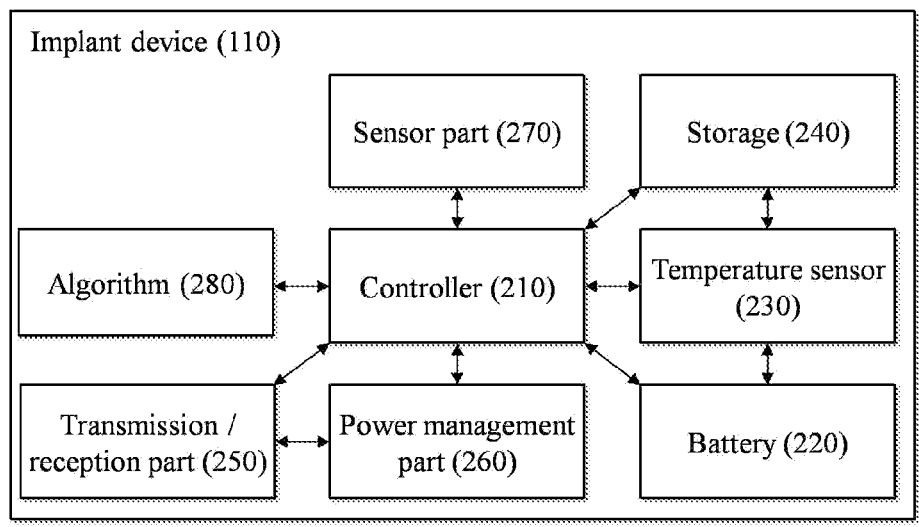
FIG. 2 is a view illustrating an example of an internal configuration of an implant device according to an embodiment of the present disclosure.

FIG. 2 is a view illustrating an example of an internal configuration of an implant device according to an embodiment of the present disclosure. The implant device 110 according to this embodiment may include a controller 210, a battery 220, a temperature sensor 230, storage 240, a transmission/reception part 250, a power management part 260, a sensor part 270, and an algorithm 280.

As explained previously, the implant device 110 may be a device inserted into an animal's body. The controller 210 may control the battery 220, the temperature sensor 230, the storage 240, the transmission/reception part 250, the power management part 260, and the sensor part 270 according to the algorithm 280.

The controller 210 may supply the battery 220's power to the temperature sensor 230 in order to continuously measure the animal's body temperature. In this case, the temperature sensor 230 may periodically measure and output the animal's internal body temperature, and the outputted internal body temperature may be cumulatively stored in the storage 240. In other words, the animal's continuous body temperature information may be stored in the storage 240.

Moreover, the controller 210 may receive wireless power from an external device outside the animal's body via the transmission/reception part 250. As explained previously, the external device according to this embodiment may refer to the external device 120 or the smart device 130 which has been explained above with reference to FIG. 1. In this case, the controller 210 may transmit the wireless power transmitted via the transmission/reception part 250 to the internal components (the battery 220, the temperature sensor 230, the storage 240, the transmission/reception part 250, the sensor part 270, and the algorithm 280) via the power management part 260. While the wireless power is being received, the power of the battery 200 may not be used, and each of the components may be operated on wireless power transmitted via the power management part 260. In some embodiments, the battery 200 may be configured in such a way as to be charged by the wireless power transmitted by the power management part 260. This may further increase the life of the battery 200.

Meanwhile, once wireless power is received, the controller 210 may send the continuous body temperature information stored in the storage 240 to the external device 120 via the transmission/reception part 250, by using the received wireless power. In other words, the implant device 110 may collect the animal's continuous body temperature information in the storage 240 via the battery 220 while no wireless power is being received, and, upon receiving wireless power, may send the animal's continuous body temperature information collected in the storage 240 to the external device outside the animal's body by using the received wireless power. This enables continuous measurement of the animal's body temperature while minimizing the power consumption of the battery 220. Moreover, the life of the battery 200 may be further increased by using wireless power to charge the battery 220.

In addition, wireless power may be used to drive a sensing circuit of the sensor part 270. For example, the control part 210 may drive the sensing circuit as the sensor part 270 by using wireless power received from the external device and measure the animal's internal biological data via the driven sensing circuit. Further, the controller 210 may calculate biological information by using the biological data measured using wireless power and send the calculated biological information to the external device via the transmission/reception part 250. Therefore, it is possible to measure and send biological information such as blood sugar levels, as well as the animal's continuous body temperature information, without consuming the battery 220. The biological information may include concentrations such as blood sugar levels and oxygen saturation, or may include numerical values from which analyte concentrations may be calculated or estimated.

To this end, the sensing circuit, as the sensor part 270, is an oscillator-type sensing circuit, and may include both a signal source and a detector. For example, the sensing circuit may include an oscillator used to produce a periodic oscillation signal. The oscillator may produce a periodic waveform with a DC power supply alone. The output waveform may be a square wave, a sine wave, or a non-sine wave according to the type of oscillator. According to an embodiment, the oscillator may include a sine wave oscillator with feedback. The feedback oscillator may be comprised of a transistor and/or amplifier (for example, OP-AMP (operational amplifier), a network of capacitors (fringing-field capacitors) and registers, a feedback component, and a gain adjusting circuit/component. Feedback is a process whereby some proportion of an output signal is passed back as input to control additional inputs.

Figure 3:
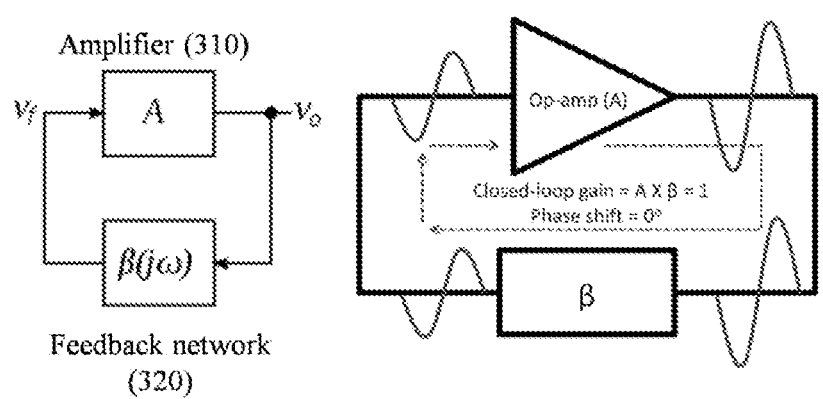
FIG. 3 is a view illustrating an example of an oscillator according to an embodiment of the present disclosure.

FIG. 3 is a view illustrating an example of an oscillator according to an embodiment of the present disclosure. The embodiment in FIG. 3 depicts an example in which some proportion of an output signal from an amplifier 310 is passed back as the input of the amplifier 310 through a feedback network 320. The feedback network may include a frequency selective filter to provide a desired phase shift. For example, a circuit for the feedback network 220 may be implemented as an RC or LC component; preferably a 3-stage RC network may be used as the feedback network 220. Although the phase shift shown in FIG. 3 is 0°, this is only an example and the phase shift angle is not limited thereto.

The oscillator may be classified according to the frequency selective filter used in the feedback network 320, and an RC oscillator is a type of feedback oscillator comprised of a network of resisters R and capacitors C.

The capacitors used in the oscillator may be mostly fringing-field capacitors which produce a fringing field. For example, an inter digited electrode type capacitor may be used.

The oscillator may be used to produce low frequencies mostly in a sub-MHz frequency range. As explained previously, an RC oscillator comprised of an RC network used to produce a phase shift needed for a response signal may be used. The RC network may be used to achieve positive feedback, causing it to generate an oscillating sinusoidal voltage and this type of oscillator has good frequency intensity, low noise, and jitter.

When power is supplied to the circuit, noise voltage starts oscillating, and the RC network shifts the phase of the output signal by 180° and routes it back as the input, generating continuous oscillations.

An LC oscillator may be comprised of an inductor L and a capacitor C, forming a tank circuit. This type of oscillator is suitable for high-frequency oscillation, but is hard to achieve a desired inductance at low frequencies in a small form factor. Accordingly, the oscillator currently used in the sensor part 110 may refer to an RC oscillator but does not preclude the use of an LC oscillator.

Figure 4:
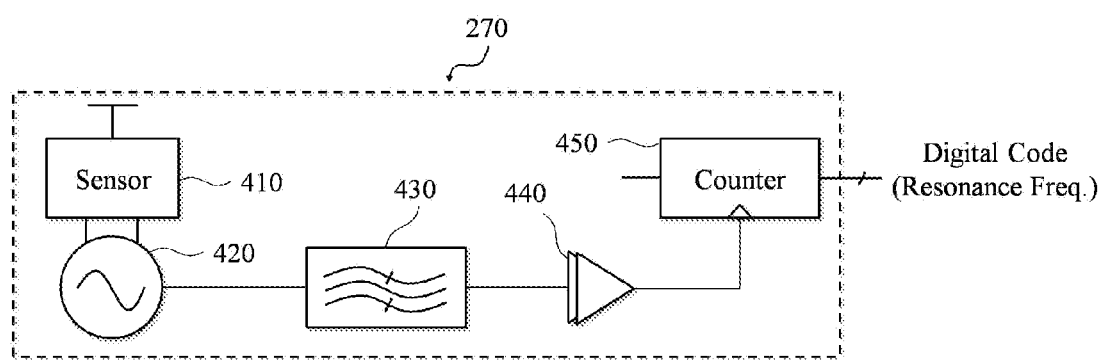
FIG. 4 is a view illustrating an example of a sensing circuit according to an embodiment of the present disclosure.

FIG. 4 is a view illustrating an example of a sensing circuit according to an embodiment of the present disclosure. The sensor part 270 according to this embodiment may include a sensor 410, an oscillator 420, a band pass filter (BPF) 430, a buffer 440, and a counter 450.

The sensor 410 may be substantially configured in such a manner as to include a fringing-field capacitor included in the oscillator 420. The fringing-field capacitor may form a fringing field, and an oscillation frequency (resonance frequency) generated by the oscillator 420 may be changed as a change in capacitance caused by a change in an analyte in the fringing field area is reflected on the oscillator 420. In this case, the sensor part 270 may measure the characteristics of the change in the analyte (for example, a change in the concentration of the analyte) in the fringing field in response to the change in the resonance frequency.

The band-pass filter 430 is a frequency selective filter that passes signals of a specific bandwidth, and signals at frequencies outside the filter specifications (for example, frequencies lower than the lower cutoff frequency of the filter and higher than the higher cutoff frequency of the filter) may be filtered out of the output of the band-pass filter 430.

The buffer 440 may be used to provide input-output matching between two different circuit components. It is a type of electrical impedance transformation from one circuit to another, which prevents signal loss. For example, the buffer 440 may provide matching between the output of the band-pass filter 430 and the input of the counter 450.

The counter 450 is a circuit that counts the frequency of a scalation signal, and may generally include a circuit for sensing zero-crossings of an input signal.

Figure 5:
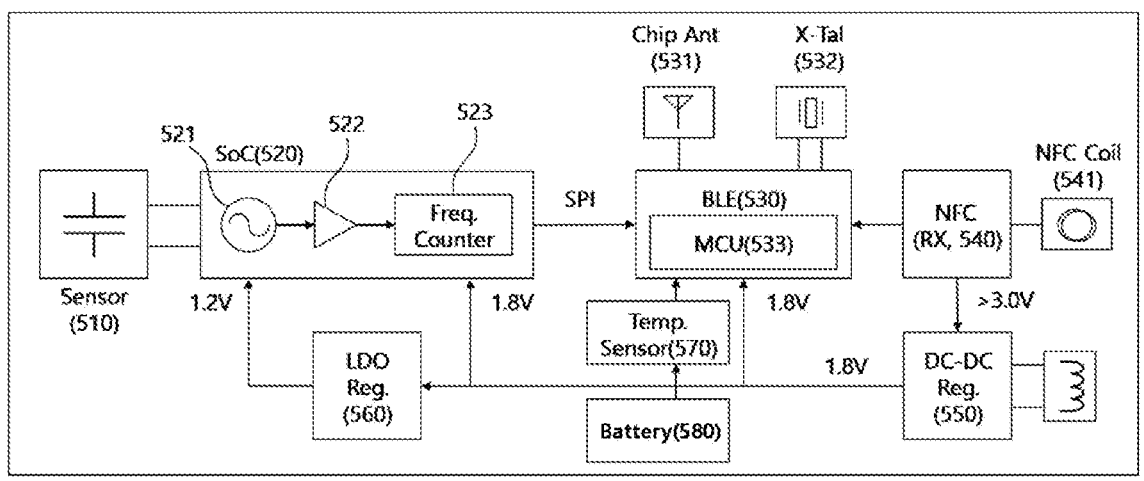
FIG. 5 to 7 are views illustrating examples of a detailed internal structure of an implant device according to an embodiment of the present disclosure.
Figure 6:
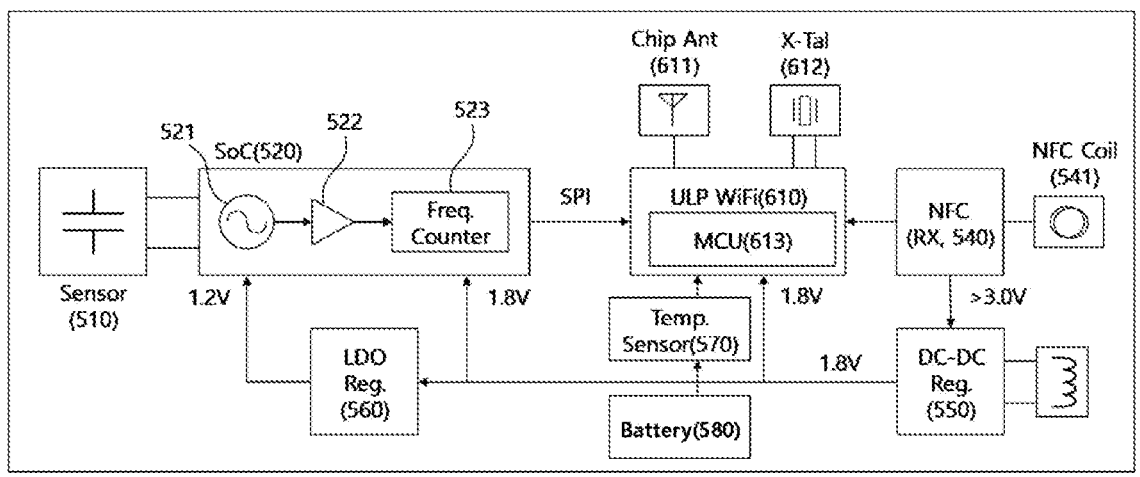
Figure 7:
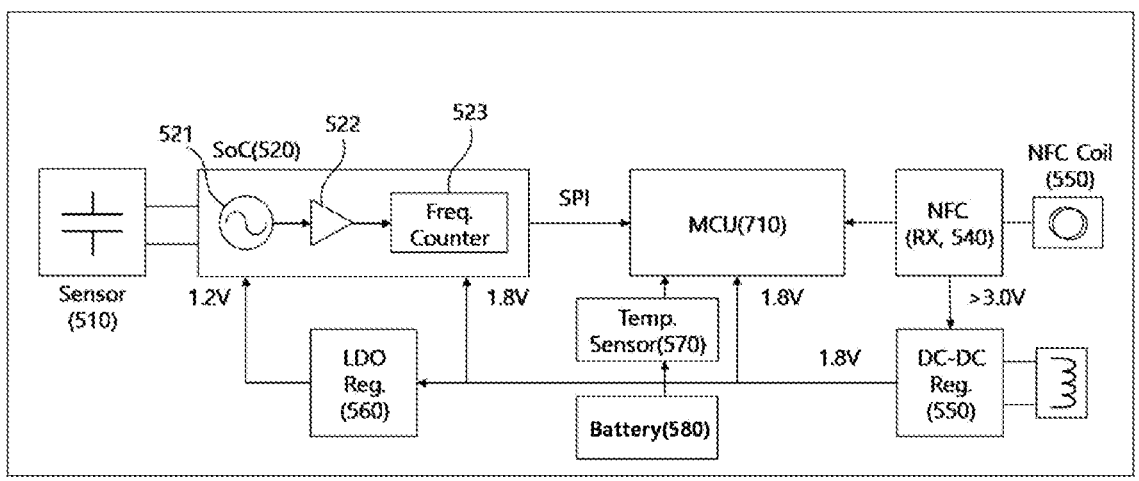

FIG. 5 to 7 are views illustrating examples of a detailed internal structure of an implant device according to an embodiment of the present disclosure.

The implant device 110 according to the embodiment in FIG. 5 may include a sensor 510, a system-on-chip (SoC) 520, BLE 530, a DC-DC regulator 550, a low drop out (LDO) regulator 560, a temperature sensor 570, and a battery 580.

The SoC 520 may include an oscillator 521, an amplifier 522, and a frequency counter (Freq. Counter) 523. The oscillator 521 may be used to produce a signal with a precise frequency, and the produced signal with that frequency may be outputted in order to measure a change in permittivity caused by a change in a surrounding target material. The sensor 510 may detect a reflected signal, and the amplifier 522 may amplify the detected signal and transmit it to the frequency counter 523. The frequency counter 523 is a circuit that calculates the frequency of a signal transmitted via the amplifier 522, which may be a circuit that detects zero-crossings of an input signal.

Detected frequency data may be sent from the SoC 520 to a micro controller unit (MCU) 533 included in the BLE 530 via a serial peripheral interface (SPI), and may be sent to the external device 120 or the smart device 130 via an antenna (2.4 GHz chip antenna (Chip Ant) 531 and/or 32 MHz X-tal 532 connected to the BLE 530.

Meanwhile, the external device 120 or the smart device 130 may transmit power for driving the implant device 110 via wireless power transmission, and near field communication (NFC) 540 included in the implant device 110 may receive power using an NFC coil 541. In this case, the NFC 540 may transmit the power of a first voltage (e.g., a voltage between 3.0 V and 5.5 V) to the DC-DC regulator 550. The DC-DC regulator 550 may convert the power of the first voltage transmitted by the NFC 540 to power of a second voltage (e.g., 1.8 V) used for an interface portion (a portion for SPI) between the MCU 533 included in the BLE 530 and the SoC 520. In the embodiment in FIG. 5, for example, power of 1.8 V is transmitted to the BLE 530 and the SoC 520. Moreover, the LDO regulator 560 may convert the power of the second voltage generated and transmitted by the DC-DC regulator 550 to power of a third voltage (e.g., 1.2 V) used for the core (the oscillator 521, the amplifier 522, and the frequency counter 523) of the SoC 520. In the embodiment in FIG. 5, for example, power of 1.2 V generated by the LDO regulator 560 is transmitted to the SoC 520.

Also, the power of the second voltage may be transmitted to the temperature sensor 570, and temperature values measured by the temperature sensor 580 also may be sent to the external device 120 or the smart device 130 via the BLE 530. As explained previously, this embodiment is described with respect to wireless power reception, and, while no wireless power is being received, the temperature sensor 570 may receive power via the battery 580, and the animal's body temperature measured by the temperature sensor 570 may be accumulated in the storage 240, so that the animal's continuous body temperature information may be generated. The continuous body temperature information stored in the storage 240 may be sent to the external device 120 or the smart device 130 via the BLE 530 by using wireless power.

Meanwhile, the implant device 110 may be controlled via the MCU 533 included in the BLE 530.

The implant device 110 according to the embodiment in FIG. 6 may include ultra low power (ULP) WiFi 610 instead of the BLE 530 mentioned in the embodiment in FIG. 5. In this case, instead of the MCU 533 included in the BLE 530, the MCU 613 included in the ULP WiFi 610 may perform the same function. Similarly to FIG. 5, the ULP WiFi 610 may be connected to an antenna (2.4 GHz chip antenna (Chip Ant) 611 and/or 32 MHz and 40 MHz X-tal 612) for communicating with the external device 120 and/or the smart device 130. For example, the MCU 613 may send frequency data sent from the SoC 520 and temperature values sent by the temperature sensor 570 to the external device 120 or the smart device 130 via an antenna. In this case, too, while no wireless power is being received, the temperature sensor 570 may receive power via the battery 580, and the animal's body temperature measured by the temperature sensor 570 may be accumulated in the storage 240, so that the animal's continuous body temperature information may be generated. The continuous body temperature information stored in the storage 240 may be sent to the external device 120 or the smart device 130 via the ULP WiFi 610 by using wireless power.

The implant device 110 according to the embodiment in FIG. 7 may include MCU 710 instead of the BLE 530 mentioned in the embodiment in FIG. 5 or the ultra low power (ULP) WiFi 610. In this case, the MCU 710 may send frequency data sent from the SoC 520 and temperature values sent by the temperature sensor 570 to the external device 120 or the smart device 130 via the NFC 540. In this case, too, while no wireless power is being received, the temperature sensor 570 may receive power via the battery 580, and the animal's body temperature measured by the temperature sensor 570 may be accumulated in the storage 240, so that the animal's continuous body temperature information may be generated. The continuous body temperature information stored in the storage 240 may be sent to the external device 120 or the smart device 130 via the NFC 540 by using wireless power.

Figure 8:
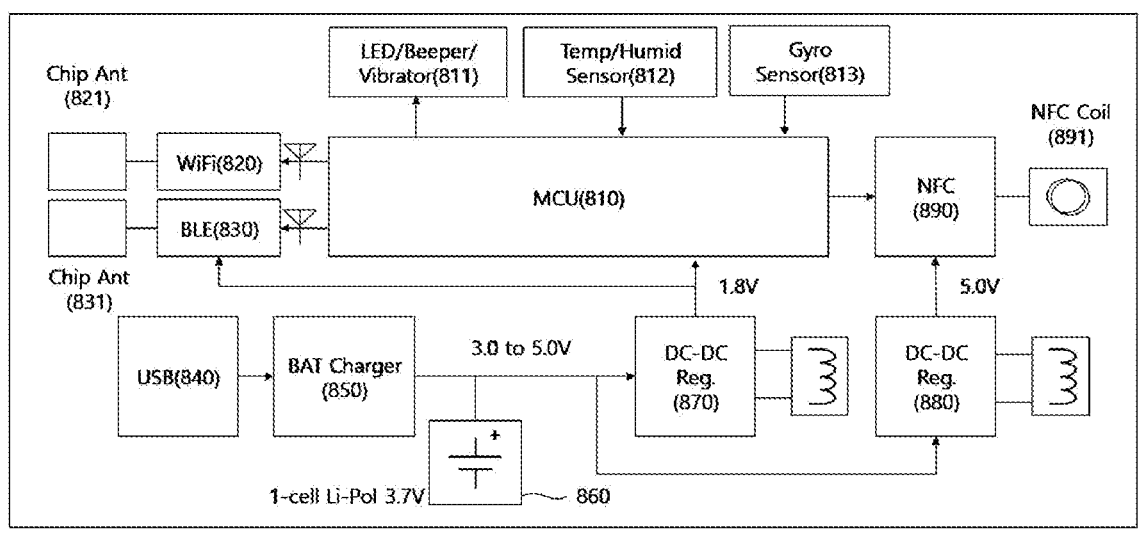
FIG. 8 is a view illustrating an example of an internal structure of an external device according to an embodiment of the present disclosure.

FIG. 8 is a view illustrating an example of an internal structure of an external device according to an embodiment of the present disclosure. The external device 120 may include MCU 810, WiFi 820, BLE 830, a universal serial bus (USB) 840, a battery charger (BAT Charger) 850, a battery 860, a first DC-DC regulator 870, a second DC-DC regulator 880, and NFC (TX) 890.

The external device 120 may be operated under control of the MCU 810. The WiFi 820 may be a WiFi module, and the external device 120 may communicate with the client server 140 using the WiFi 820 under control of the MCU 810. Similarly, the external device 120 may communicate with the implant device 110 using the BLE 830 under control of the MCU 810. To this end, the WiFi 820 and the BLE 830 may be respectively connected to antennas (for example, 2.4 GHz chip antennas 821 and 831). The WiFi 820 and the BLE 830 are only an example and do not limit the present disclosure. For example, as explained previously, the WiFi 820 may be used to communicate with the implant device 110, or a 5th-generation mobile communication technology may be used for communication with the client server 140. In some embodiments, the WiFi 820 and the BLE 830 may be used in order for the external device 120 to communicate with the smart device 130.

The battery 860 may be charged via the USB 840 and the battery charger 850. For example, the battery 860 may be, but not limited to, a 1-cell 3.7V lithium polymer battery. Power of a fourth voltage (e.g., voltage between 3.0 V and 5.0 V) may be transmitted to the first DC-DC regulator 870 and the second DC-DC regulator 880 via the battery charger 850 or the battery 860. The first DC-DC regulator 870 may convert the power of the fourth voltage to power of a fifth voltage (e.g., 1.8 V) and transmit it to the MCU 810, the WiFi 820, and the BLE 830. Also, the second DC-DC regulator 880 may convert the power of the fourth voltage to power of a sixth voltage (e.g., 5.0 V) and transmit it to the NFC (TX) 890. The NFC 890 may be transmitted to the implant device 110 via the NFC coil 891.

Meanwhile, the external device 120 may further include an output device 811, a temperature/humidity sensor (Temp/Humid sensor) 812, and/or a gyro sensor 813.

For example, the MCU 810 may be connected to the output device 811 to provide visual, audio, and/or tactile information to the user. As illustrated in FIG. 8, such an output device 811 may include, but not limited to, a light-emitting diode (LED), a beeper, and/or a vibrator. Such an output device 811 may be used to provide an alert notification to the user.

Moreover, the MCU 810 may be connected to the temperature/humidity sensor 812. While the foregoing temperature sensor 570 included in the implant device 110 is used to measure animal body temperature, the temperature/humidity sensor 812 may be used to measure information on the surroundings outside of the animal's body. Temperature values and/or humidity values measured by the temperature/humidity sensor 812 may be sent to the implant device 110, the smart device 130, and/or the cloud server 140 via the MCU 810, the WiFi 820, and the BLE 830.

In addition, the MCU 810 may be connected to the gyro sensor 813. The gyro sensor 813 may be used to generate the animal's activity information based on the angular velocity of the external device 120. It should be easily understood that, although the foregoing embodiment has been described with respect to the smart device 130 generating activity information and sending it to the implant device 110, the external device 120 may provide activity information to the implant device 110 based on the gyro sensor 813.

Meanwhile, the smart device 130, the cloud server 140, and the plurality of family devices 151 to 153 may be configured by at least one computer device.

Figure 9:
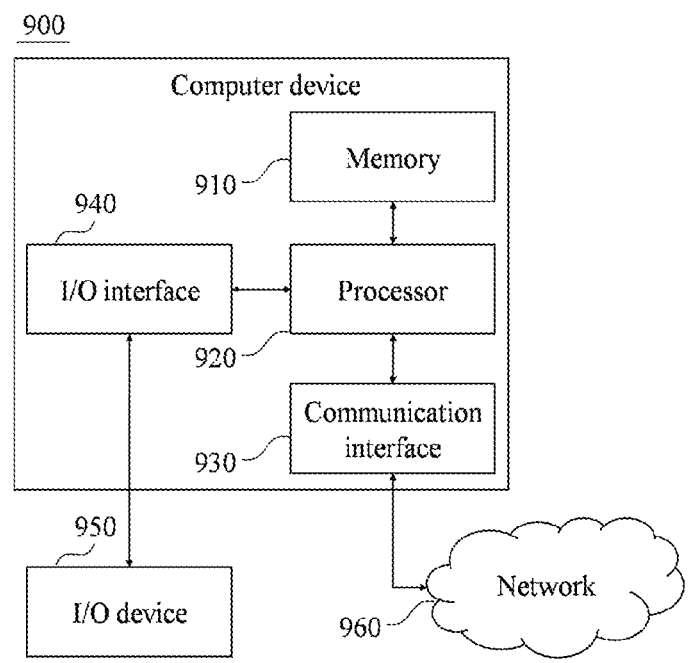
FIG. 9 is a block diagram illustrating an example of a computer device according to an embodiment of the present disclosure.

FIG. 9 is a block diagram illustrating an example of a computer device according to an embodiment of the present disclosure. As illustrated in FIG. 9, the computer device 900 may include a memory 910, a processor 920, a communication interface 930, and an I/O interface 940.

The memory 910 is a computer-readable recording medium, and may include a permanent mass storage device such as a random access memory (RAM), a read only memory (ROM) and a disk drive. Here, the permanent mass storage device, such as a ROM and a disk drive, may be included in the computer device 900 as a permanent storage device separate from the memory 910. Moreover, an operating system and at least one program code's may be stored in the memory 910. Such software elements may be loaded onto the memory 910 from a computer-readable recording medium separate from the memory 910. Such a separate computer-readable recording medium may include computer-readable recording media, such as a floppy drive, a disk, a tape, a DVD/CD-ROM drive, and a memory card. In another embodiment, software elements may be loaded onto the memory 910, not via a computer-readable recording medium, but via the communication interface 930. For example, the software elements may be loaded onto the memory 910 of the computer device 900 based on a computer program installed by files received over a network 960. The network 960 may include the network 160 explained with reference to FIG. 1.

The processor 920 may be configured to process instructions of a computer program by performing basic arithmetic, logic and I/O operations. The instructions may be provided to the processor 920 by the memory 910 or the communication interface 930. For example, the processor 920 may be configured to execute instructions received according to program code stored in a recording medium such as the memory 910.

The communication interface 930 may provide a function for enabling the computer device 900 to communicate with other devices over the network 960. For example, a request, a command, data or a file generated by the processor 920 of the computer device 900 according to program code stored in a recording device, such as the memory 910, may be sent to other devices over the network 960 under control of the communication interface 930. Inversely, a signal, a command, data or a file from another device may be received by the computer device 900 via the communication interface 930 of the computer device 900 over the network 960. A signal, a command, or data received via the communication interface 930 may be sent to the processor 920 or the memory 910, and a file received via the communication interface 930 may be stored in a storage medium (the aforementioned permanent storage device) which may be further included in the computer device 900.

The I/O interface 940 may be a means for interfacing with an input/output (I/O) device 950. For example, input devices such as a microphone, a keyboard, a camera, or a mouse may be included, and output devices such as a display or speaker may be included. For another example, the I/O interface 940 may be a means for interfacing with such a device as a touchscreen whose input and output functions are combined. The I/O device 950 may be integrated with the computer device 900.

Furthermore, in other embodiments, the computer device 900 may include more or fewer components than those shown in FIG. 9. However, it is not necessary to clearly illustrate most of conventional components. For example, the computer device 900 may be configured to include at least some of the above I/O devices 950, or may further include other components like a transceiver or a database.

FIG. 10 is a flowchart illustrating an example of a method for continuously measuring animal body temperature by an implant device according to an embodiment of the present disclosure.

In the step 1010, the implant device 110 may periodically measure an animal's body temperature by a temperature sensor by using battery power. It is difficult to measure an animal's core body temperature outside the animal's body, and even harder to continuously measure body temperature. In view of this, the implant device 110 may be inserted into the animal's body, and may include a battery to continuously measure the animal's body temperature within the animal's body. The implant device 110 may periodically measure the animal's body temperature by a temperature sensor by using the battery's power. The battery and the temperature sensor may correspond to the battery 220 and temperature sensor 230 explained previously with reference to FIG. 2 and/or the battery 580 and temperature sensor 570 explained previously with reference to FIGS. 5 to 7.

In the step 1020, the implant device 110 may store continuous body temperature information in storage. Periodical body temperature measurements taken by the temperature sensor may be stored in the storage. The storage may correspond to the storage 240 explained previously with reference to FIG. 2. As the periodical body temperature measurements are accumulated in the storage, the animal's continuous body temperature information may be generated and stored in the storage.

In the step 1030, the implant device 110 may receive wireless power from an external device outside the animal's body. For example, the implant device 110 may receive wireless power using near field communication (NFC). The external device according to this embodiment may include the external device 120 or smart device 130 explained previously with reference to FIG. 1.

In the step 1040, the implant device 110 may send the continuous body temperature information stored in the storage to the external device by using the received wireless power. In an embodiment, the implant device 110 may send the continuous body temperature information to the external device via the NFC. In this case, both a transmission part and a reception part may be configured via the NFC. In this case, however, the implant device 110 may include a separate MCU for implementing the controller 210 and operate under control of the MCU. In another embodiment, the implant device 110 may include Bluetooth low energy (BLE) or ultra low power (ULP) WiFi and operate under control of the MCU included in the BLE or ULP WiFi. In this case, the implant device 110 may send the continuous temperature information to the external device via an antenna connected to the BLE or the ULP WiFi. In other words, the reception part may be configured with the NFC, and the transmission part may be configured with the BLE or the ULP WiFi. In this instance, the MCU included in the BLE or ULP WiFi may serve as the controller 210 of the implant device 110.

Meanwhile, the battery may be configured to be charged by wireless power. In other words, when wireless power is received, the implant device 110 may increase the life of the battery of the implant device 110 inserted into the animal's body by charging the battery by wireless power.

Moreover, the steps 1010 to 1040 describe a process for continuously measuring and sending animal body temperature. The subsequent steps 1050 to 1080 describe a process for measuring and sending additional biological information.

In the step 1050, the implant device 110 may drive a sensing circuit using the wireless power received from the external device. In this instance, the sensing circuit is an oscillator-type sensing circuit, and may include both a signal source and a detector.

In the step 1060, the implant device 110 may measure the animal's internal biological data via the driven sensing circuit. For example, the implant device 110 may generate a fringing field by using the sensing circuit, measure a change in a resonance frequency generated by an oscillator based on a change in capacitance caused by a change in an analyte in the fringing field area, and measure the characteristics of the change in the analyte in the fringing field, as the biological data, in response to the change in the resonance frequency. These characteristics of the change in the analyte may refer to the characteristics of a change in the concentration of the analyte.

In this instance, the implant device 110 may generate a fringing field by a fringing-field capacitor of the oscillator which is included as the sensing circuit. Also, the implant device 110 may generate a periodic oscillation signal by using a feedback network, which includes the fringing-field capacitor of the oscillator, as the sensing circuit, and a frequency selective filter, and which passes back some portion of an output signal as input to provide a desired phase shift. In this case, the implant device 110 may measure the characteristics of the change in the analyte within the fringing field in response to the change in the resonance frequency by measuring a change in capacitance caused by a change in permittivity by means of a sensing part including a material with a dielectric constant.

In the step 1070, the implant device 110 may calculate biological information using the measured biological data. In some embodiments, the implant device 110 may calculate the biological information by further using current body temperature information, among the continuous body temperature information, since the biological information may be affected by temperature.

In the step 1080, the implant device 110 may further send the calculated biological information to the external device by using the wireless power. In other words, once wireless power is received from the external device, the implant device 110 may measure biological information and send to the external device the measured biological information, along with the continuous body temperature information stored in the storage.

In this way, according to the embodiments of the present disclosure, an implant device inserted into an animal's body is able to continuously measure body temperature within an animal's body and minimize the battery power consumption of the implant device, by continuously measuring and storing the animal's body temperature information using battery power and sending the stored continuous body temperature information to an external device outside the animal's body using wireless power from the external device. Moreover, it is possible to detect the concentration of an analyte by sensing a change in capacitance caused by a change in the analyte present in a fringing field area and sensing and measuring a change in a resonance frequency generated by an oscillator.

The aforementioned system or device may be implemented as a hardware component, a software component and/or a combination of a hardware component and a software component. For example, the device and components described in the embodiments may be implemented using one or more general-purpose computers or special-purpose computers, for example, a processor, a controller, an arithmetic logic unit (ALU), a digital signal processor, a microcomputer, a field programmable gate array (FPGA), a programmable logic unit (PLU), a microprocessor or any other device capable of executing or responding to an instruction. A processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary knowledge in the art may understand that the processing device may include a plurality of processing components and/or a plurality of types of processing components. For example, the processing device may include a plurality of processors or one processor and one controller. Furthermore, other processing configurations, such as a parallel processor, are also possible.

Software may include a computer program, a code, an instruction or a combination of one or more of them, and may configure a processor so that it operates as desired or may instruct processors independently or collectively. Software and/or data may be embodied in any type of a machine, component, physical device, virtual equipment, or computer storage medium or device so as to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure alone or in combination. The program instructions stored in the medium may be specially designed and constructed for the present disclosure, or may be known and available to those skilled in the field of computer software. Examples of the computer-readable storage medium include magnetic media such as a hard disk, a floppy disk and a magnetic tape, optical media such as a CD-ROM and a DVD, magneto-optical media such as a floptical disk, and hardware devices specially configured to store and execute program instructions such as a ROM, a RAM, and a flash memory. Examples of the program instructions include not only machine language code that is constructed by a compiler but also high-level language code that can be executed by a computer using an interpreter or the like.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned components, such as the system, configuration, device, and circuit, are coupled or combined in a form different from that of the described method or replaced or substituted with other components or equivalents.

Accordingly, other implementations, other embodiments, and the equivalents of the claims fall within the scope of the claims.

The invention claimed is:

1. A system for continuously measuring animal body temperature, the system comprising:
an external device for transmitting wireless power into an animal's body from outside the animal's body comprising a humidity sensor configured to measure a humidity value from a location outside of the animal's body and a gyro sensor configured to generate an animal activity information based on an angular velocity of the external device, wherein the humidity sensor and the gyro sensor are configured to send the humidity value and the animal activity information, respectively, to an implant device;
the implant device inserted into the animal's body, that periodically measures the animal's body temperature by a temperature sensor by using battery power and stores body temperature information in storage, and that, when wireless power is received from the external device, sends the body temperature information stored in the storage to the external device by using the received wireless power; and
a sensing circuit driven by the implant device using the wireless power received from the external device, wherein the sensing circuit is a sine oscillator with a feedback network, and wherein the implant device generates a fringing field by using a sensing circuit, measures a change in a resonance frequency generated by an oscillator based on a change in capacitance caused by a change in an analyte in the fringing field area, and measures the characteristics of the change in the analyte in the fringing field in response to the change in the resonance frequency by measuring a change in capacitance caused by a change in permittivity by means of a sensing part including a material with a dielectric constant, and wherein the sensing circuit comprises:
an amplifier configured to amplify and transmit a reflected signal by the fringing field to a frequency counter; and
the frequency counter, wherein the frequency counter is a circuit configured to calculate a frequency of the reflected signal and detect a zero-crossing of the reflected signal.

2. The system of claim 1, wherein the implant device receives the wireless power using near field communication (NFC) and sends the body temperature information to the external device via the NFC.

3. The system of claim 1, wherein the implant device comprises Bluetooth low energy (BLE) or ultra low power (ULP) WiFi, operates under control of a micro controller unit (MCU) included in the BLE or ULP WiFi, and sends the body temperature information to the external device via an antenna connected to the BLE or the ULP WiFi.

4. The system of claim 1, wherein the implant device drives the sensing circuit using the wireless power received from the external device, measures the animal's internal biological data via the driven sensing circuit, calculates biological information using the measured biological data, and further sends the calculated biological information to the external device by using the received wireless power.

5. The system of claim 4, wherein the implant device calculates the biological information by further using current body temperature information, among the body temperature information.

6. The system of claim 4, wherein the sensing circuit comprises both a signal source and a detector.

7. The system of claim 1, wherein the implant device generates the fringing field by a fringing-field capacitor of the oscillator which is included as the sensing circuit.

8. The system of claim 1, wherein the implant device generates a periodic oscillation signal by using the feedback network, which includes the fringing-field capacitor of the oscillator, as the sensing circuit, and a frequency selective filter, and which passes back some portion of an output signal as input to provide a desired phase shift.

9. The system of claim 1, wherein the battery is configured to be charged by the wireless power.

10. An implant device inserted into an animal's body to measure body temperature, the implant device comprising:
a controller;
a battery;
a temperature sensor;
a transmission/reception part wherein the transmission/reception part is configured to receive a humidity value and an animal activity information, from a humidity sensor and a gyro sensor, respectively; and
a sensing circuit, wherein the sensing circuit is a sine oscillator with a feedback network,
wherein the controller periodically measures the animal's body temperature by the temperature sensor by using the battery's power and stores body temperature information in storage, and, when wireless power is received from an external device, sends the body temperature information stored in the storage to the external device via the transmission/reception part by using the received wireless power, and drives a sensing circuit using the wireless power received from the external device, and wherein the implant device generates a fringing field by using a sensing circuit, measures a change in a resonance frequency generated by an oscillator based on a change in capacitance caused by a change in an analyte in the fringing field area, and measures the characteristics of the change in the analyte in the fringing field in response to the change in the resonance frequency by measuring a change in capacitance caused by a change in permittivity by means of a sensing part including a material with a dielectric constant, and wherein the sensing circuit comprises:
an amplifier configured to amplify and transmit a reflected signal by the fringing field to a frequency counter; and
the frequency counter, wherein the frequency counter is a circuit configured to calculate a frequency of the reflected signal and detect a zero-crossing of the reflected signal.

11. The implant device of claim 10, wherein the transmission/reception part comprises near field communication (NFC), and the controller receives the wireless power using the NFC and sends the body temperature information to the external device using the NFC.

12. The implant device of claim 10, wherein the transmission/reception part comprises a transmission part and a reception part,
wherein the transmission part comprises Bluetooth low energy (BLE) or ultra low power (ULP) WiFi, and the controller is implemented by a micro controller unit (MCU) included in the BLE or ULP WiFi to send the body temperature information to the external device via an antenna connected to the BLE or the ULP WiFi.

13. The implant device of claim 10, wherein the controller further drives the sensing circuit using the wireless power received from the external device, measures the animal's internal biological data via the driven sensing circuit, calculates biological information using the measured biological data, and further sends the calculated biological information to the external device via the transmission/reception part by using the wireless power.

14. The implant device of claim 10, wherein the battery is configured to be charged by the wireless power.

15. A method for continuously measuring animal body temperature by an implant device inserted into an animal's body, the method comprising the steps of:
periodically measuring the animal's body temperature by a temperature sensor by using battery power;
storing body temperature information in storage;
receiving wireless power from an external device outside the animal's body;
receiving a humidity value and an animal activity information, from a humidity sensor and a gyro sensor, respectively;
storing the humidity value and the animal activity information in storage;
sending the body temperature information, humidity value, and animal activity information stored in the storage to the external device by using the received wireless power;
generating a fringing field by using the sensing circuit;
measuring a change in a resonance frequency generated by an oscillator based on a change in capacitance caused by a change in an analyte in the fringing field area;
measuring the characteristics of the change in the analyte in the fringing field in response to the change in the resonance frequency by measuring a change in capacitance caused by a change in permittivity by means of a sensing part including a material with a dielectric constant; and
driving a sensing circuit using the wireless power received from the external device, wherein the sensing circuit is a sine oscillator with a feedback network, and wherein the sensing circuit comprises:
an amplifier configured to amplify and transmit a reflected signal by the fringing field to a frequency counter; and
the frequency counter, wherein the frequency counter is a circuit configured to calculate a frequency of the reflected signal and detect a zero-crossing of the reflected signal.

16. The method of claim 15, wherein the receiving step comprises receiving the wireless power using near field communication (NFC), and the transmitting step comprises sending the body temperature information to the external device via the NFC.

17. The method of claim 15, wherein the implant device comprises Bluetooth low energy (BLE) or ultra low power (ULP) WiFi and operates under control of a micro controller unit (MCU) included in the BLE or ULP WiFi,
wherein, in the transmitting step, the implant device sends the body temperature information to the external device via an antenna connected to the BLE or the ULP WiFi.

18. The method of claim 15, further comprising the steps of:
measuring the animal's internal biological data via the driven sensing circuit;
calculating biological information using the measured biological data; and
further sending the calculated biological information to the external device by using the wireless power.

* * * * *